United States Patent [19]

Takahashi

[11] Patent Number: 4,581,939
[45] Date of Patent: Apr. 15, 1986

[54] NONCONTACT ULTRASONIC FLAW DETECTING METHOD AND APPARATUS THEREFOR

[75] Inventor: Fuminobu Takahashi, Katsuta, Japan

[73] Assignee: Hitachi, Ltd., Tokyo, Japan

[21] Appl. No.: 620,021

[22] Filed: Jun. 13, 1984

[30] Foreign Application Priority Data

Jun. 15, 1983 [JP] Japan ................. 58-105651

[51] Int. Cl.$^4$ ............ G01N 29/04; G01H 9/00
[52] U.S. Cl. ....................... 73/643; 73/655; 73/657
[58] Field of Search ............ 73/643, 655, 656, 657; 356/358

[56] References Cited

U.S. PATENT DOCUMENTS

| | | | |
|---|---|---|---|
| 3,978,713 | 9/1976 | Penney | 73/643 |
| 4,046,477 | 9/1977 | Kaule | 73/643 |
| 4,121,469 | 10/1978 | Kaule et al. | 73/643 |
| 4,169,662 | 10/1979 | Kaule et al. | 73/643 |
| 4,246,793 | 1/1981 | Fairand et al. | 73/643 |
| 4,345,475 | 8/1982 | Bickel | 73/655 |
| 4,388,832 | 6/1983 | Kaule | 73/655 |
| 4,448,525 | 5/1984 | Mikoshiba et al. | 73/643 |
| 4,484,820 | 11/1984 | Rosencwaig | 73/643 |

Primary Examiner—Howard A. Birmiel
Attorney, Agent, or Firm—Antonelli, Terry & Wands

[57] ABSTRACT

The surface of a specimen to be inspected is irradiated with a light having an intensity which varies from a position distant from the material, so that ultrasonic beams are generated in the material to be inspected. A coherent light is also projected onto a fixed surface provided at a given position and onto the surface of said material to be inspected. Vibration generated in the surface of said material due to ultrasonic beams reflected by a defect in the material, is detected in the form of change in phase of the coherent light that is reflected by the surface of the material. The change of difference in phase between the coherent light reflected by said fixed surface and the coherent light reflected by the surface of the material is measured with the lapse of time, in order to detect the flaw.

8 Claims, 18 Drawing Figures

NONCONTACT ULTRASONIC FLAW DETECTING METHOD AND APPARATUS THEREFOR

BACKGROUND OF THE INVENTION

1. Field of the Invention

The present invention relates to a noncontact ultrasonic flaw detecting method and an apparatus therefor, and particularly to a noncontact ultrasonic flaw detecting method utilizing ultrasonic waves generated in materials, wherein the materials to be inspected, such as steel members are irradiated with a laser beam or the like to detect flaws therein and to an apparatus therefor.

2. Description of the Prior Art

A conventional noncontact ultrasonic flaw detecting method comprises steps of instantaneously irradiating a material such as steel member to be inspected with a laser beam, generating ultrasonic waves in the material to be inspected, and generating thermal impact in the irradiated portion of the material (U.S. Pat. No. 4,137,778).

According to the above-mentioned noncontact ultrasonic flaw detecting method wherein the material to be inspected is simply irradiated with a laser beam, the accuracy for detecting a flaw is low since ultrasonic waves are not focused in the material being inspected and the propagation direction is not controlled.

With the contact-type ultrasonic flaw detecting method wherein an ultrasonic probe is pressed on the surface of the material to detect a flaw, an angled ultrasonic wave beam or a focused ultrasonic wave beam is generated in the material to be inspected, in order to detect flaw therein.

However, when the material to be inspected is heated at high temperatures, the ultrasonic probe may be damaged by the heat. Since water, glycerin, oil or the like existing in a space between the ultrasonic probe and the surface of the material to be inspected evaporates, it is difficult to correctly detect a flaw in the material. With this method, furthermore, it is not possible to detect a flaw in the material that is heated higher than a predetermined temperature, or to detect a flaw in the material from a remote position.

SUMMARY OF THE INVENTION

The object of the present invention is to provide a noncontact ultrasonic flaw detecting method and an apparatus therefor, according to which the propagation direction or focusing of ultrasonic waves generated in the material to be inspected is controlled, and the condition of defects is detected relying upon the interference of light, to highly accurately detect a flaw in the material.

A feature of the present invention resides in a noncontact ultrasonic flaw detecting method according to which the surface of a material to be inspected is irradiated with a light having changing irradiation intensity, to generate ultrasonic waves in the material to be inspected, a coherent light and another coherent light which is reflected by the surface of the material to be inspected are projected onto predetermined positions, and a change of difference in phase between the coherent light and another coherent light which is reflected is measured in dependence upon time, in order to detect a flaw in the material being inspected.

Another feature of the present invention resides in a noncontact ultrasonic flaw detecting apparatus comprising light irradiation means which irradiates the surface of the material to be inspected with the light having varying intensity; a first coherent light generating means which is disposed on the material to be inspected, and which generates a first coherent light; a second coherent light generating means which generates a second coherent light that is incident upon, and reflected by, the surface of the material to be inspected; and a light measuring means which measures the change of difference in phase between the first coherent light and the second coherent light in dependence upon time.

Namely, according to the present invention, the surface of a material to be inspected is irradiated with light which has varying intensity and which is emitted from a position remote from the material. Further, a fixed surface at a given position and the surface of the material to be inspected are irradiated with coherent lights, respectively. Vibration produced on the surface of the material by ultrasonic waves reflected from defects in the material, is detected in the form of a change in phase of the coherent light that is reflected by the surface of the material, and the change of difference in phase between the coherent light reflected from the fixed surface and the coherent light reflected from the surface of the material is measured to detect a flaw.

According to the present invention, the propagation direction, focusing or non-focusing condition of ultrasonic waves generated in the material to be inspected can be controlled, and the condition of defects can be detected relying upon the interference of light, making it possible to detect a flaw highly accurately.

DETAILED DESCRIPTION OF THE INVENTION

Described below are a principle for generating an ultrasonic wave beam that plays an important role for the noncontact ultrasonic flaw detection of the present invention, and a principle for detecting a flaw, by using light ultrasonic waves reflected by defects in the material that is to be inspected.

First, described below is a principle for generating an ultrasonic wave beam, which can be considered as one based upon a light irradiation pattern by spatially changing the irradiation intensity, and another based upon the irradiation of light by changing the irradiation intensity with regard to time.

An example is described below to determine the propagation direction of a focused ultrasonic wave beam using a pattern of light irradiation having an intensity that changes spatially.

Figure 1:
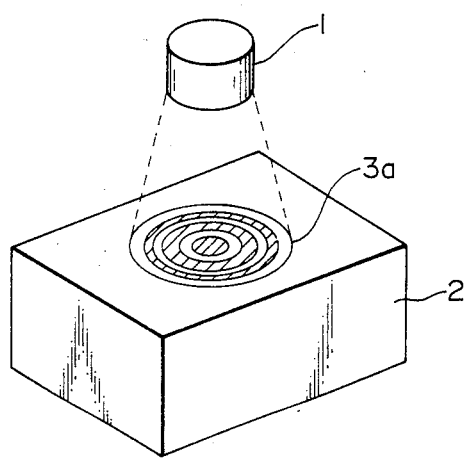
FIG. 1 is a diagram of a principle of a method of light irradiation for generating a vertically focusing ultrasonic wave beam.

As shown in FIG. 1, the surface of a specimen 2 (or a material to be inspected) is instantaneously irradiated with the light emitted from a source of light 1. The distribution of light intensities is expressed as a concentric Fresnel ring pattern 3a. Hatched portions of the Fresnel ring pattern 3a represent areas where intense light is received, and white portions represent areas where weak intensity of light is received. Strong thermal impact is applied to the hatched portions of the Fresnel ring pattern 3a to generate ultrasonic waves.

Figure 2:
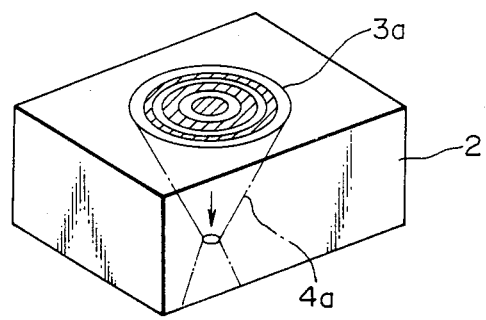
FIG. 2 is a diagram illustrating a relation between the irradiation pattern and the ultrasonic wave beam of FIG. 1.

Ultrasonic waves generated in each of the portions are interfered by each other in the specimen 2, and form a vertically focused ultrasonic wave beam 4a having a propagation direction which focuses at a point on an extension at the center portion of the Fresnel ring pattern 3a, as indicated by a dot-dash line in FIG. 2.

Figure 3:
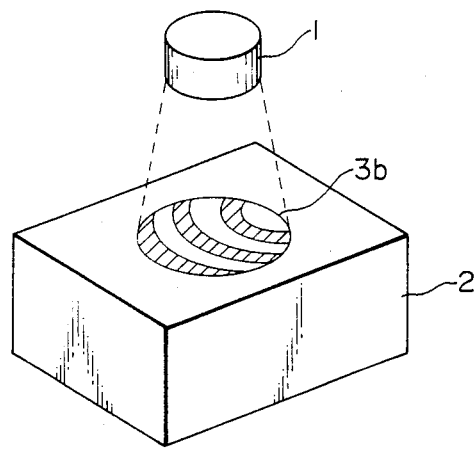
FIG. 3 is a diagram of a principle of a method of light irradiation for generating an obliquely focusing ultrasonic wave beam.

As shown in FIG. 3, furthermore, the distribution of light intensities may also be expressed as a ring pattern 3b which does not contain the center of the Fresnel ring pattern 3a of FIG. 1.

Figure 4:
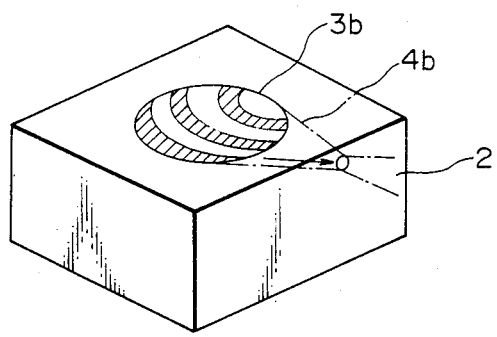
FIG. 4 is a diagram illustrating a relation between the irradiation pattern and the ultrasonic wave beam of FIG. 3.

In this case, the ultrasonic waves which are generated form an obliquely or angled focused ultrasonic wave beam 4b having a propagation direction that focuses at a point on an extension at the center of the ring pattern 3b, as indicated by a dot-dash line in FIG. 4.

Described below is an example for determining the propagation direction of an ultrasonic wave beam by the irradiation of light with an intensity changing in regard to time.

Figure 5:
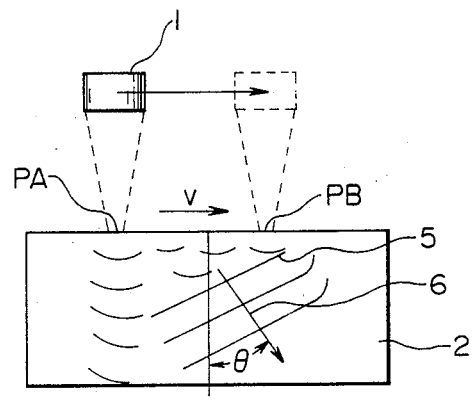
FIG. 5 is a diagram of a principle for generating an oblique ultrasonic wave beam by moving the position of light irradiation.

The light to be irradiated may be moved. Namely, as shown in FIG. 5, the source of light 1 is moved to move the position of light irradiation from a point PA to a point PB at a speed v. In this case, there are generated ultrasonic waves spherically from the surface of the specimen 2 that is successively irradiated with the light. The ultrasonic waves spherically generated from each of the positions along the way from the position PA to the position PB are interfered by each other to form phase planes 5, whereby the ultrasonic waves propagate in a direction indicated by arrow 6.

An angle (incident angle) $\theta$ between the propagation direction and a normal drawn to the surface of the specimen 2 is given by, $$\theta = \arcsin(v/v_a) \tag{1}$$

where $v_a$ denotes the speed of sound in the specimen 2.

Thus, the position of light irradiation is moved to change the incident angle of ultrasonic waves. In other words, an ultrasonic wave beam having a propagation direction in the specimen 2 is generated by irradiating the surface of the specimen 2 with the light of which the intensity changes with the lapse of time.

Described below is a principle for detecting the ultrasonic waves reflected by defects in the specimen by using light.

Figure 6:
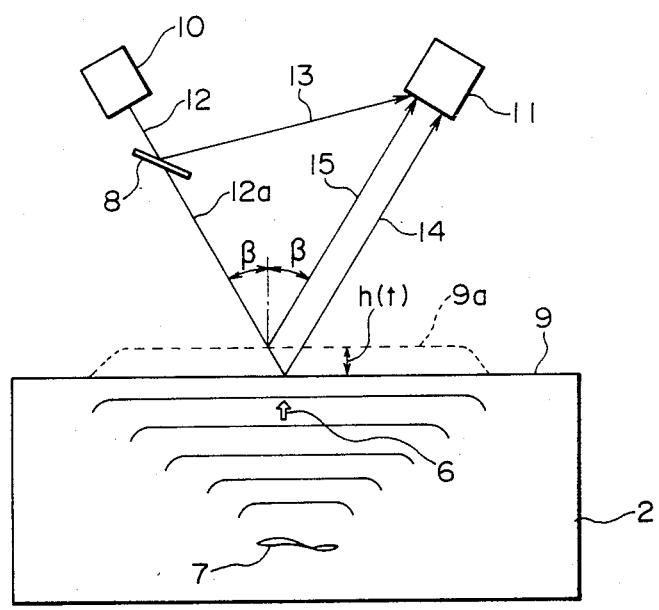
FIG. 6 is a diagram of a principle for detecting ultrasonic waves utilizing the light.

As shown in FIG. 6, a first coherent light 12 emitted from a source of light 10 is partly reflected by a half mirror 8 and is permitted to be incident upon a light detector 11 via a path 13. On the other hand, a second coherent light 12a which has passed through the half mirror 8 is reflected by the surface of the specimen 2 and is allowed to be incident upon the light detector 11 via a path 14.

As the ultrasonic waves reflected in the direction of arrow 6 by a defect 7 in the specimen 2 reach the surface of the specimen 2, the surface of the specimen 2 undergoes a vibration with the displacement as indicated by a dotted line 9a. The displacement with the lapse of time is indicated by h(t). The coherent light 12a is reflected by the displaced surface 9a, and is made incident upon the light detector 11 via a path 15.

Therefore, the light detector 11 measures the change in the intensity of light depending upon the displacement h(t) of the surface of the specimen 2 with the lapse of time, i.e., depending upon the difference in phase between the first coherent light 12 and the second coherent light 12a that is reflected, which changes with the lapse of time. The reasons will be described below.

If the distance of the path 13 is denoted by $l_r$ and the distance of the path 14 by $l_0$, then the distance $l(t)$ of the path 15 is given by, $$l(t) = l_0 - 2h(t) \cos\beta \tag{2}$$

where $\beta$ denotes an incident angle of light upon the surface of the specimen 2.

If the coherent light reaching the light detector 11 via path 13 is denoted by $\phi_r$ and the coherent light reaching the light detector 11 via path 15 by $\phi_0$, then the wave motions of these light rays are expressed as follows:

$$\phi_r = C_r e^{-ikl_r} \tag{3}$$

$$\phi_0 = C_0 e^{-ikl(t)} \tag{4}$$

where k denotes a wave number of the light.

The light detector 11 detects the interfering intensity $\phi_i$ between lights light of $\phi_r$ and $\phi_0$. The interfering intensity $\phi_i$ is given by the following equation, $$\phi_i = \phi_r^* \cdot \phi_0 + \phi_r \cdot \phi_0^* = 2C_0C_r\cos[K(l(t) - l_r)] \\ = 2C_0C_r\cos[K(-2h(t)\cos\beta + l_0 - l_r)] \tag{5}$$

where symbol * denotes a complex conjugate.

As represented by the equation (5), it will be recognized that the interfering intensity $\phi_i$ detected by the light detector 11 changes depending upon the displacement h(t) of the surface of the specimen 2 caused by the ultrasonic waves with the lapse of time, i.e., changes depending upon the difference in phase between the coherent light $\phi_r$ and the coherent light $\phi_0$, that varies with the lapse of time.

Figure 7:
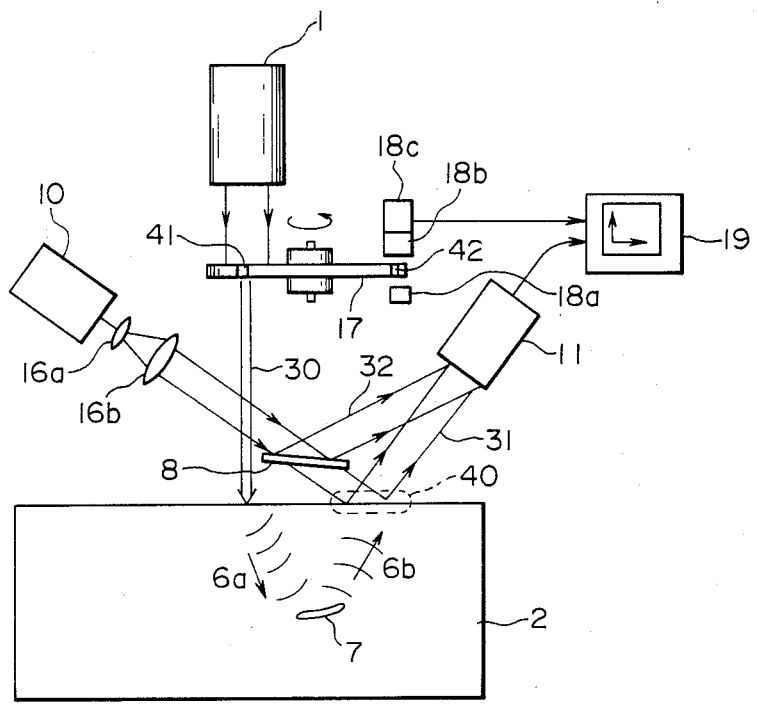
FIG. 7 is a schematic diagram for illustrating a first embodiment of the present invention.

An embodiment (first embodiment) of the present invention will be described below. As shown in FIG. 7, a ray of light 30 which is a portion of light flux emitted from the source of light 1 passes through a light chopper 17 in the form of a light-shielding member, and falls on the surface of the specimen 2. The position of irradiating light 30 is successively changed with the lapse of time by the light chopper 17.

The ultrasonic beam generated in the specimen 2 propagates in a direction 6a, and is reflected by the internal defect 7 in a direction 6b. The reflected ultrasonic beam vibrates on the surface of the specimen 2 at a region 40.

The light emitted from a laser device 10 is transformed into parallel beams through two lenses 16a, 16b, and is guided to the half mirror 8. A coherent light 32 reflected by the half mirror 8 is incident directly upon the light detector 11, and a coherent light 31 which has transmitted through the half mirror 8 is reflected by the region 40 and is incident upon the light detector 11 which sends an interfering intensity of the coherent light 32 and coherent reflected light 31 to a waveform observation instrument 19.

In this embodiment, a photomultiplier tube is used as the light detector 11, and a synchroscope is used as the waveform observation instrument 19.

A trigger generator 18c sends a trigger signal to the waveform observation instrument 19 just as the light chopper 17 permits the ray of light 30 to pass through. That is, as the ray of light 30 is to be transmitted, the light emitted from a photodiode 18a is received by a light sensor 18b via an aperture 42 (see FIG. 9) formed in the light chopper 17, and the trigger generator 18c produces a trigger signal responsive to the received signal.

The waveform observation instrument 19 displays the input signal from the light detector 11 which changes with the lapse of time, with the trigger signal from the light chopper 17 as a starting point (reference value for time measurement).

Figure 8:
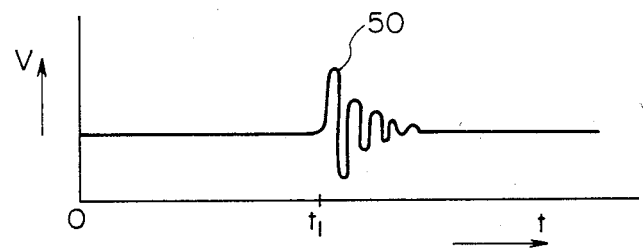
FIG. 8 is a diagram showing a signal produced by a light detector of FIG. 7.
Figure 9A:
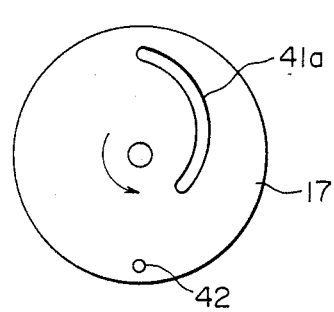
FIGS. 9(a), 9(b), 9(c) and 9(d) are plan views of light choppers used in the first embodiment.
Figure 9B:
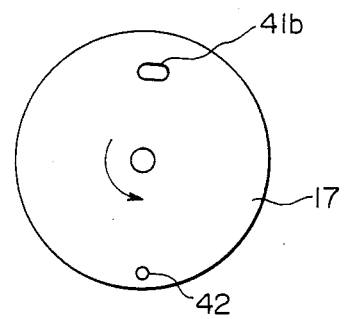
Figure 9C:
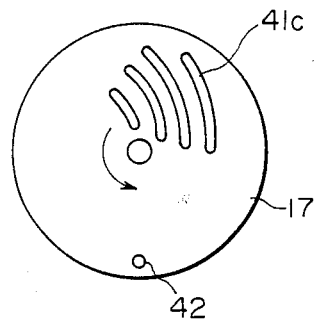
Figure 9D:
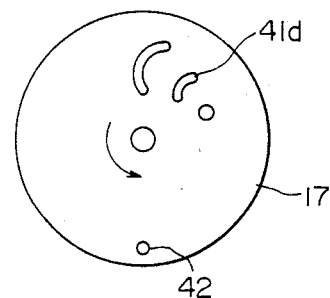

FIG. 8 shows an example of signal waveform displayed on the waveform observation instrument 19, wherein the ordinate represents the voltage V and the abscissa represents the time t. At a time $t_1$, a pulse signal 50 is reflected by the defect 7.

The light detector 11 detects the phase difference between the coherent light 32 reflected by the half mirror 8 and the coherent light 31 reflected by the surface of the specimen 2, as the intensity of light.

Therefore, the reflected light should desirably be detected as a spot light via lenses. However, the reflected light may be focused once on the screen to detect the intensity of the image.

A variety of ultrasonic beams can be produced through the light chopper 17 by selecting openings 41 that are formed in the light chopper 17 and that permit the passage of light.

FIGS. 9(a)-(d) are plan views which illustrate representative examples of the openings 41 formed in the light chopper 17. An obliquely directed or angled ultrasonic wave beam is generated by using an opening 41a shown in FIG. 9(a), a vertically directed or angled ultrasonic beam is generated by using an opening 41b shown in FIG. 9(b), an obliquely or angled focused ultrasonic beam is generated by using openings 41c shown in FIG. 9(c), and a vertically focused ultrasonic beam is generated by using openings 41d shown in FIG. 9(d).

Figure 10:
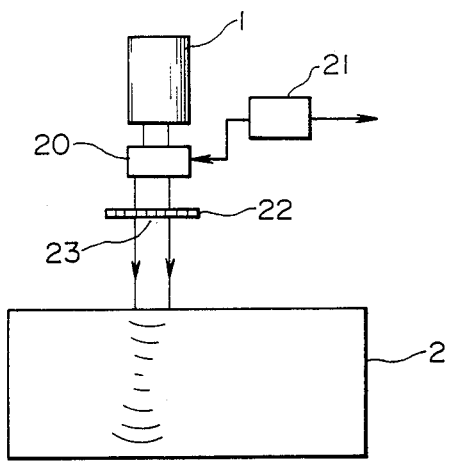
FIG. 10 is a diagram showing a major portion of light irradiation means according to a second embodiment.

Another embodiment (second embodiment) of the present invention will be described below. This embodiment is different from the first embodiment with regard to the structure of light irradiation means which generates an ultrasonic beam in the specimen 2. FIG. 10 shows a main portion of the second embodiment, i.e., shows the structure of this light irradiation means.

The light emitted from the light source 1 passes through a light switch 20, and only the light which has passed through a lattice 23 of a shielding lattice plate 22 is allowed to fall on the surface of the specimen 2. Here, the light-shielding member consists of the light switch 20 and the shielding lattice plate 22. The light switch 20 permits the light to pass through instantaneously in synchronism with a signal from the pulse generator 21.

Figure 11A:
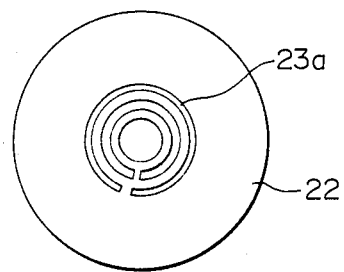
FIGS. 11(a) and 11(b) are plan views of light-shielding plates used in the second embodiment.
Figure 11B:
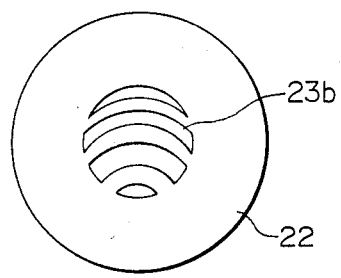

The vertically foscused ultrasonic beam and the obliquely focused ultrasonic beam can be generated if lattices 23a, 23b shown in FIGS. 11(a) and 11(b) are used for the shielding lattice plate 22 in the light irradiation means.

Figure 12:
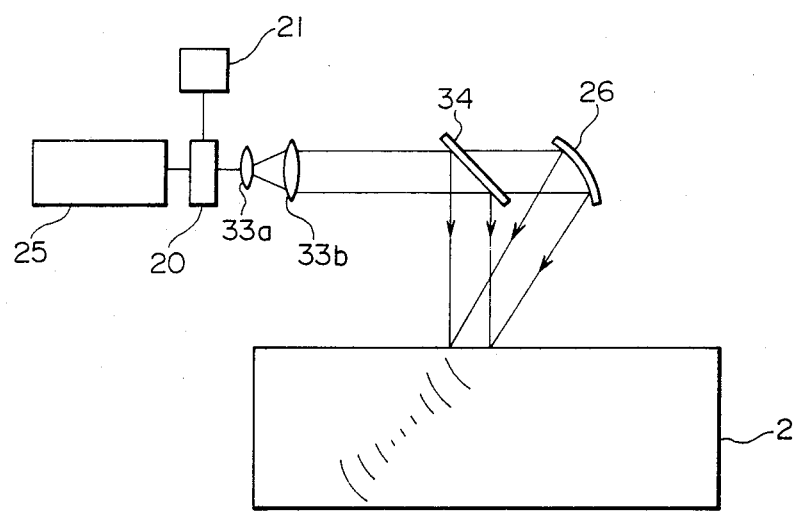
FIG. 12 is a schematic diagram showing means for generating an obliquely focusing ultrasonic wave beam according to a third embodiment.

A further embodiment (third embodiment) of the present invention will be described below. This embodiment is different from the first embodiment only with respect to the light irradiation means which generates ultrasonic beams in the specimen 2. FIG. 12 shows a main portion of the third embodiment, i.e., shows the light irradiation means.

The light from a high-output laser device 25 is permitted to pass instantaneously through the light switch 20 which opens in response to a pulse signal sent from the pulse generator 21, and is allowed to pass through two lenses 33a and 33b to form parallel rays of light. One-half of the parallel rays of light is projected on the surface of the specimen 2 by a half mirror 34, and another half of the parallel rays of light is projected on the surface of the specimen 2 by a spherical lens 26.

The two rays of light are interfered by each other on the irradiated surface of the specimen 2, to form a pattern which is shown in FIG. 4. Consequently, the obliquely focusing ultrasonic beam is generated in the specimen 2.

Figure 13:
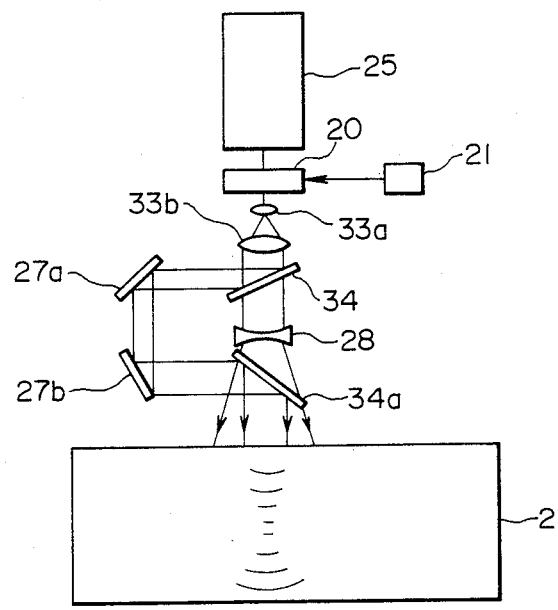
FIG. 13 is a schematic diagram showing means for generating a vertically focusing ultrasonic wave beam according to a fourth embodiment.

A fourth embodiment of the present invention will be described. This embodiment is different from the first embodiment only with regard to the light irradiation means. FIG. 13 shows the light irradiation means.

The light irradiation means of this embodiment consists of the structure of the third embodiment, being further provided with a half mirror 34a, a concave lens 28, and two mirrors 27a and 27b.

If the rays of light expanded by the concave lens 28 and the parallel rays of light reflected by the half mirror 34a are interfered by each other on the surface of the specimen 2, the intensity of irradiated light forms a Fresnel ring pattern as shown in FIG. 2. In this case, the vartically focused ultrasonic beam is generated in the specimen 2.

Figure 14:
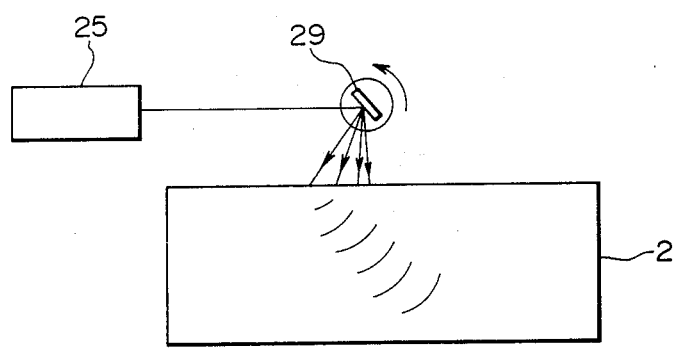
FIG. 14 is a schematic diagram showing means for generating ultrasonic waves using a rotary mirror according to a fifth embodiment.

A fifth embodiment of the present invention will be explained below. This embodiment is also different from the first embodiment only with regard to the light irradiation means which generates ultrasonic beams in the specimen 2. FIG. 14 shows the light irradiation means.

A rotary mirror 29 is rotated to scan the light emitted from the laser device 25 on the surface of the specimen 2. The rotary mirror 29 produces the same effect as when the source of light is moved in FIG. 5. Namely, the obliquely directed or angled ultrasonic beam is generated in the specimen 2.

The obliquely directed non-focused ultrasonic wave beam will be obtained when the rotary mirror 29 comprises a plate mirror, and the obliquely or angled focused ultrasonic wave beam will be obtained when the rotary mirror 29 comprises a convex mirror.

What is claimed is:

1. A noncontact ultrasonic flaw detecting method comprising the steps of:
    irradiating a surface of a material to be inspected with an irradiating light;
    changing an intensity of the irradiating light to generate one of angled and foscused ultrasonic waves in the material to be inspected so that a flaw in the material to be inspected causes the generated ultrasonic waves to be reflected therefrom and cause vibration at a region of the surface of the material to be inspected;
    projecting a first coherent light directly onto a surface of a detector from a light source;
    projecting from the light source a second coherent light onto the surface of the material to be inspected so that the second coherent light is reflected from the surface of the material onto the surface of the detector; and
    measuring a time dependent interference intensity between the first coherent light and the second coherent light reflected from the vibrating surface region of the material to be inspected so as to direct a flaw in the material to be inspected.

2. A noncontact ultrasonic flaw detecting method according to claim 1, wherein the step of changing the intensity of the irradiating light includes rotating a light-shielding member having openings therein in an optical path of the irradiating light so as to permit passage of the irradiating light therethrough in order to spatially change the irradiation intensity of the irradiating light.

3. A noncontact ultrasonic flaw detecting method according to claim 1, wherein the step of changing the intensity of the irradiating light includes instantaneously irradiating with the irradiating light a light-shielding member having openings in an optical path of the irradiating light for permitting the passage of the irradiating light therethrough so as to spatially change the intensity of the irradiating light.

4. A noncontact ultrasonic flaw detecting method according to claim 1, wherein the step of changing the intensity of the irradiating light includes transforming the irradiation light into a plurality of light rays, irradiating the surface of the material to be inspected with a first portion of the light rays, reflecting a remaining portion of the light rays by at least one reflector so as to irradiate the surface of the material to be inspected with the remaining portion of the light rays of light, and interfering the light rays of the first portion and remaining portion with each other on the surface of the material to be inspected.

5. A noncontact ultrasonic flaw detecting apparatus comprising:
    means for irradiating the surface of a specimen to be inspected with light which varies in intensity so as to generate one of angled and focused ultrasonic waves in the material to be inspected so that a flaw in the material to be inspected causes the generated ultrasonic waves to be reflected therefrom and cause vibration at a region of the surface of the material to be inspected;
    means for generating coherent light;
    light detector means;
    means responsive to the coherent light generating means for directing a first coherent light directly onto a surface of the light detector means and for projecting a second coherent light onto the surface of the material to be inspected so that the second coherent light is reflected from the surface of the material onto the surface of the light detector means; and
    measuring means responsive to the light detector means for measuring a time dependent interference intensity between the first coherent light and the second coherent light reflected from the vibrating surface region of the material to be inspected so as to detect a flaw in the material to be inspected.

6. A noncontact ultrasonic flaw detecting apparatus according to claim 5, wherein the light irradiating means comprises a light source and a rotatable light-shielding member having openings therein in an optical path of the irradiating light from the light source so as to permit passage of the irradiating light therethrough.

7. A noncontact ultrasonic flaw detecting apparatus according to claim 5, wherein the light irradiating means comprises a light source, light switching means for instantaneously permitting the passage of light emitted from the light source therethrough, and means for causing at least two rays of light passing through the light switch means to interfere with each other on the surface of the material to be inspected.

8. A noncontact ultrasonic flaw detecting apparatus according to claim 5, wherein the light measuring means measures the light intensity received by the light detecting means which varies in accordance with time and which corresponds to the displacement of the surface of the material to be inspected, the displacement being caused by the reflection of the ultrasonic waves from a flaw.

* * * * *